United States Patent [19]
Berg et al.

[11] Patent Number: 6,019,874
[45] Date of Patent: Feb. 1, 2000

[54] SEPARATION OF CONJUGATED LINOLEIC ACIDS BY AZEOTROPIC DISTILLATION

[76] Inventors: Lloyd Berg, 1314 S. 3rd. Ave., Bozeman, Mont. 59715; Terry Brix, P.O. Box 190, Blue River, Oreg. 97413

[21] Appl. No.: 09/232,902

[22] Filed: Jan. 19, 1999

[51] Int. Cl.[7] .......................................................... B01D 3/36

[52] U.S. Cl. .............................................................. 203/61

[58] Field of Search ...................................... 203/60.01, 61

[56] References Cited

U.S. PATENT DOCUMENTS

| | | | |
|---|---|---|---|
| 4,874,473 | 10/1989 | Arit et al. | 203/1 |
| 5,391,264 | 2/1995 | Berg | 203/57 |
| 5,582,693 | 12/1996 | Berg | 203/57 |
| 5,698,080 | 12/1997 | Berg | 203/57 |

*Primary Examiner*—James H. Reamer

[57] ABSTRACT

Conjugated linoleic acids cannot be separated by distillation or rectification because of the closeness of their boiling points. Conjugated linoleic acids can be separated by azeotropic distillation. Effective agents are butyraldehyde, butyl ether and 1-methyl-2-pyrrolidinone.

1 Claim, No Drawings

SEPARATION OF CONJUGATED LINOLEIC ACIDS BY AZEOTROPIC DISTILLATION

FIELD OF THE INVENTION

This invention relates to a method for separating conjugated linoleic acids by azeotropic distillation.

DESCRIPTION OF PRIOR ART

Azeotropic distillation is the method of separating close boiling compounds or azeotropes from each other be carrying out the distillation in a multiplate rectification column in the presence of an added liquid, said liquid forming an azeotrope with one or more of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

Conjugated linoleic acids boil only one degree apart and have a relative volatility of 1.05 which makes it impossible to separate them by conventional distillation or rectification. Table 2 shows that with an agent giving a relative volatility of 1.26, only 52 actual plates are required to get 99% purity.

TABLE 2

Theoretical And Actual Plates Required vs. Relative Volatility For Conjugated Linoleic Acids Sepatation

| Relative Volatilty | Theoretical Plates Required At Total Reflux, 99% Purity | Actual Plates Required, 75% Efficiency |
|---|---|---|
| 1.14 | 70 | 94 |
| 1.16 | 62 | 83 |

TABLE 2-continued

Theoretical And Actual Plates Required vs. Relative Volatility For Conjugated Linoleic Acids Sepatation

| Relative Volatilty | Theoretical Plates Required At Total Reflux, 99% Purity | Actual Plates Required, 75% Efficiency |
|---|---|---|
| 1.26 | 40 | 53 |
| 1.27 | 39 | 52 |

OBJECTIVE OF THE INVENTION

The object of this invention is to provide a process or method of azeotropic distillation that will enhance the relative volatility of conjugated linoleic acids in their separation in a rectification column. It is a further object of this invention to identify effective azeotropic distillation agents that are stable and can be recycled.

SUMMARY OF THE INVENTION

The objects of this invention are provided by a process for the separation of conjugated linoleic acids which entails the use of certain organic compounds when employed as the agent in azeotropic distillation.

TABLE 3

Effective Azeotropic Distillation Agents For Separatuin Of Conjugated Linoleic Acids By

| | Relative Volatility |
|---|---|
| None | 1.05 |
| Ethyl acetoacetate | 1.14 |
| Propiophenone | 1.16 |
| Butyraldehyde | 1.26 |
| Butyl ether | 1.25 |
| 1-Methyl-2-pyrrolidinone | 1.25 |

WORKING EXAMPLE

Example 1; Fifty grams of conjugated linoleic acids mixture and fifty grams of butyl ether as the azeotropic forming agent were charged to a vapor-liquid equilibrium still and refluxed for two hours. The vapor composition was 50% 1-conjugated linoleic acid, 50% 2-conjugated linoleic acid; the liquid composition was 55.6% 1-conjugated linoleic and 44.4% 2-conjugated acid. This is a relative volatility of 1.25.

We claim:

1. A method for separating a mixture of conjugated linoleic acids which comprises distilling a mixture of conjugated linoleic acids in the presence of an azeotropic forming agent, recovering 1-conjugated linoleic and the azeotrope forming agent as overhead product and obtaining the 2-conjugated linoleic acid as bottoms product, wherein said azeotrope forming agent consists essentially of one material selected from the group consisting of propiophenone, ethyl acetate, butyraldehyde, butyl ether and 1-methyl-2-pyrrolidinone.

* * * * *